United States Patent [19]

Dörreich et al.

[11] Patent Number: 5,624,835
[45] Date of Patent: Apr. 29, 1997

[54] ENDO-β-1,4-GLUCANASE AND A DNA SEQUENCE

[75] Inventors: Kurt Dörreich, Grenzach-Wyhlen, Germany; Flemming M. Christensen, Rungsted Kyst, Denmark; Yvette Schnell, Roschenz; Marcel Mischler, Himmelried, both of Switzerland; Henrik Dalbøge; Hans P. Heldt-Hansen, both of Virum, Denmark

[73] Assignee: Novo Nordisk A/S, Bagsvaerd, Denmark

[21] Appl. No.: 313,073

[22] PCT Filed: Mar. 26, 1993

[86] PCT No.: PCT/DK93/00108

§ 371 Date: Oct. 5, 1994

§ 102(e) Date: Oct. 5, 1994

[87] PCT Pub. No.: WO93/20193

PCT Pub. Date: Oct. 14, 1993

[30] Foreign Application Priority Data

Mar. 27, 1992 [DK] Denmark ................. 0419/92

[51] Int. Cl.$^6$ .............. C12N 9/42; C12N 15/56; C12N 15/74; C12N 15/80
[52] U.S. Cl. .......... 435/204; 435/69.1; 435/252.3; 435/254.3; 435/320.1; 536/23.2; 536/23.74; 935/14; 935/28
[58] Field of Search ............. 435/69.1, 204, 435/252.3, 252.31, 252.33, 320.1, 267; 536/23.2, 23.74

[56] References Cited

FOREIGN PATENT DOCUMENTS

| | | |
|---|---|---|
| 0495258 | 7/1992 | European Pat. Off. . |
| 89-09259 | 10/1989 | WIPO . |
| 91-17244 | 11/1991 | WIPO . |
| 91-17243 | 11/1991 | WIPO . |
| 94-14953 | 7/1994 | WIPO . |

OTHER PUBLICATIONS

Törrönen, A., et al., 1993, FEBS Letters, 321(2-3):135–139.
Dalbøge, H., et al., 1994, Molecular and General Genetics 243:253–260.
Williamson, G., et al., 1990, Carbohydrate Polymers, 13:387–397.
Ooi et al., Nucleic Acids Research, vol. 18, No. 19, p. 5884 (1990).
Murao et al., Agric. & Biological Chemistry, vol. 49, pp. 3511–3518 (1985).
Arai et al., Agric. & Biological Chemistry, vol. 51, pp. 627–633 (1987).
Ooi, T., et al., 1990, Current Genetics, 18:217–222.
Harkki, A., et al., 1991, Enzyme & Microbiol Technology, 13:227–233.
Sakamoto, R., et al., 1984, Journal of Fermentation Technology, 62(6):561–567.
Sakamoto, R., et al., 1985, Agricultural and Biological Chemistry, 49(5):1283–1290.
Yoshizumi, A., et al., 1987, Trends in Biotechnology 5(10):277–281.

Primary Examiner—Robert A. Wax
Assistant Examiner—William W. Moore
Attorney, Agent, or Firm—Steve T. Zelson, Esq.; James Harrington, Esq.

[57] ABSTRACT

The molecular characteristics and a partial amino acid sequence of an endo-β-1,4-glucanase obtainable from *Aspergillus aculeatus* are described, as well as corresponding recombinant DNA sequences, vectors, and transformed hosts. Use of the endo-β-1,4-glucanase or a pectinase preparation enriched with the endo-β-1,4-glucanase for degradation or modification of plant cell walls is described.

12 Claims, 11 Drawing Sheets

5,624,835

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ala Ser Val Phe Glu Trp Ile Gly Ser Asn Glu Ser Gly Ala Glu Phe
1               5                   10                  15

Gly Thr Ala
```

( 2 ) INFORMATION FOR SEQ ID NO: 2:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

```
CAGTCGACAG  GCACCATGAA  GCTGCTTAAC  CTACTTGTTG  CTGCTGCCGC  GGCCGGCAGT        60
```

( 2 ) INFORMATION FOR SEQ ID NO: 3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 3:

```
GCAGTGGCGG  CCCCGACCCA  CGAACACACG  AAGCGGGCTT  CTGTTTTCGA  ATGGATCGGA        60
```

( 2 ) INFORMATION FOR SEQ ID NO: 4:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 4:

```
TCCAATGAGT  CGGGCGCCGA  GTTCGGCACC  GCATTCGGAA  CTTGGGGTAT  CGACT             55
```

( 2 ) INFORMATION FOR SEQ ID NO: 5:

( i ) SEQUENCE CHARACTERISTICS:
        ( A ) LENGTH: 175 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 5:

```
CAGTCGACAG  GCACCATGAA  GCTGCTTAAC  CTACTTGTTG  CTGCTGCCGC  GGCCGGCAGT        60

GCAGTGGCGG  CCCCGACCCA  CGAACACACG  AAGCGGGCTT  CTGTTTTCGA  ATGGATCGGA       120

TCCAATGAGT  CGGGCGCCGA  GTTCGGCACC  GCATTCGGAA  CTTGGGGTAT  CGACT            175
```

1

ENDO-β-1,4-GLUCANASE AND A DNA SEQUENCE

CROSS-REFERENCE TO RELATED APPLICATIONS

This application is a continuation of PCT/DK93/00108 filed Mar. 25, 1993, which is incorporated herein by reference.

The invention comprises an endo-β-1,4-glucanase, a corresponding DNA sequence, a vector, a transformed host, a method for production of an endo-β-1,4-glucanase, an enzyme preparation, and a use of the endo-/β-1,4-glucanase.

The invention relates to genetic engineering and provides a partial amino acid sequence of an endo-β-1,4-glucanase and partial DNA sequences.

Endo-β-1,4-glucanases (EC no. 3.2.1.4) is a group of hydrolases, which catalyse endo hydrolysis of 1,4-β-D-glycosidic linkages in cellulose, lichenin, cereal β-D-glucans and other plant material containing cellulosic pans. The authorized name is endo-1,4-β-D-glucan 4-glucano hydrolase, but the short term endo-β-1,4-glucanase is used in this specification with claims. Reference can be made to R. F. Gould, "Cellulases and their Application", Advances in Chemistry Series 55, American Chemical Society (1969), T. M. Wood, "Properties and Mode of Action of Cellulases", in Biotechnology and Bioengineering Symposium, no. 5, John Wiley, 111–137 (1975), Y.-H. Lee and L. T. Fan, "Properties and Mode of Action of Cellulose", Advances in Biochemical engineering 17, 101–129 (1980), J. Gokseyr and J. Eriksen, "Cellulases" in A. H. Rouse, Microbial Enzymes and Bioconversions, Academic Press, 283–330 (1980), T.-M. Enveri, "Microbial Cellulases" in W. M. Fogarty, Microbial Enzymes and Biotechnology, Applied Science Publishers, 183–224 (1983). Celluloses are found in connection with many gums and they are components of cell walls in e.g. fruits, vegetables and cereals.

The above indicated partial amino acid sequence can be used for construction of DNA probes which can be used for screening a genomic library for organisms expressing such enzyme, or a cDNA library, thereby obtaining DNA sequences, which can be used either for an overproduction of endo-β-1,4-glucanase, if inserted in the microorganism species, from which the parent DNA molecule originated, or for production of endo-β-1,4-glucanase without accompanying closely related enzymes, if inserted in a host microorganism, which in its not-transformed condition does not produce any enzymes closely related to endo-β-1,4-glucanase. The DNA sequences can be established otherwise, as will appear from the following.

Thus, the purpose of the invention is the provision of a new endo-β-1,4-glucanase and of means and methods for production of endo-β-1,4-glucanase in better yield and higher purity than hitherto possible, and of a use of endo-β-1,4-glucanase either alone or in combination with other enzymes for degradation of plant cell wall tissue, more efficient than hitherto possible. Also it is the purpose of the invention to provide novel products, wherein the proportion of the endo-β-1,4-glucanase is either increased or decreased in relation to the proportion in the original product.

The recombinant DNA sequence obtainable according to the invention comprises a DNA sequence coding for a polypeptide having endo-β-1,4-glucanase activity, or a DNA sequence having substantial sequence homology to such endo-β-1,4-glucanase coding sequence.

The endo-β-1,4-glucanase according to the invention is characterized by the fact that it is immunologically reactive with an antibody raised against a purified endo-β-1,4-glucanase derived from Aspergillus aculeatus, CBS 101.43.

In the present context the term "derived from" is intended not only to indicate an endo-β-1,4-glucanase produced by strain CBS 101.43, but also an endo-β-1,4-glucanase encoded by a DNA sequence isolated from strain CBS 101.43 and produced in a host organism transformed with said DNA sequence.

Figure 10:
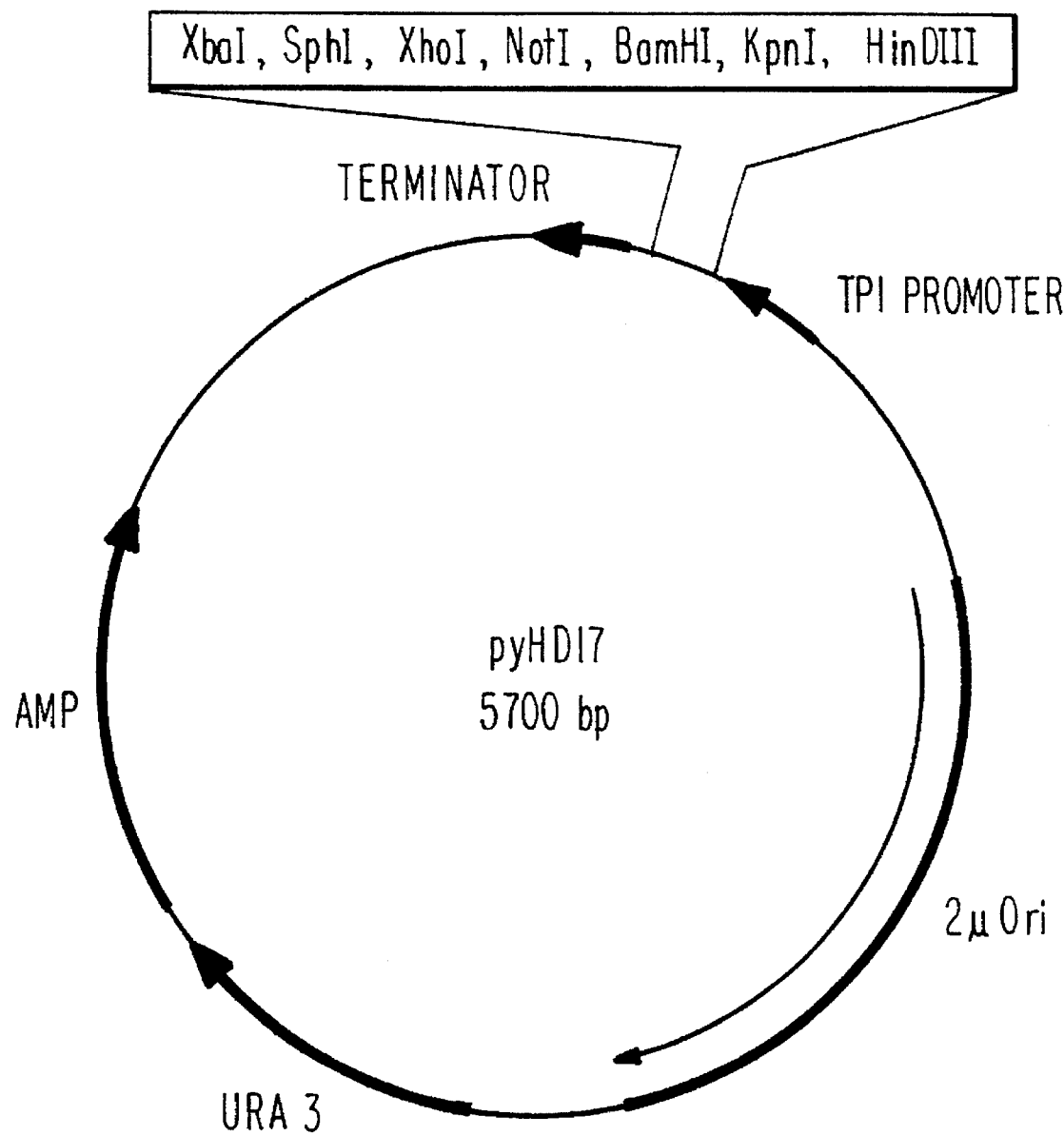

FIG. 10 shows a map of plasmid pYHD17, wherein "TPI promotor" indicates the Saccharomyces cerevisiae triose phosphate isomerase promotor, "Terminator" indicates the transcription terminator, "Amp" indicates the gene mediating ampicillin resistance, "2u-ORI" indicates the yeast plasmid 2u origin of replication, and "URA3" indicates a gene encoding a selection marker complementing a uracil deficiency in the host strain.

Figure 11:
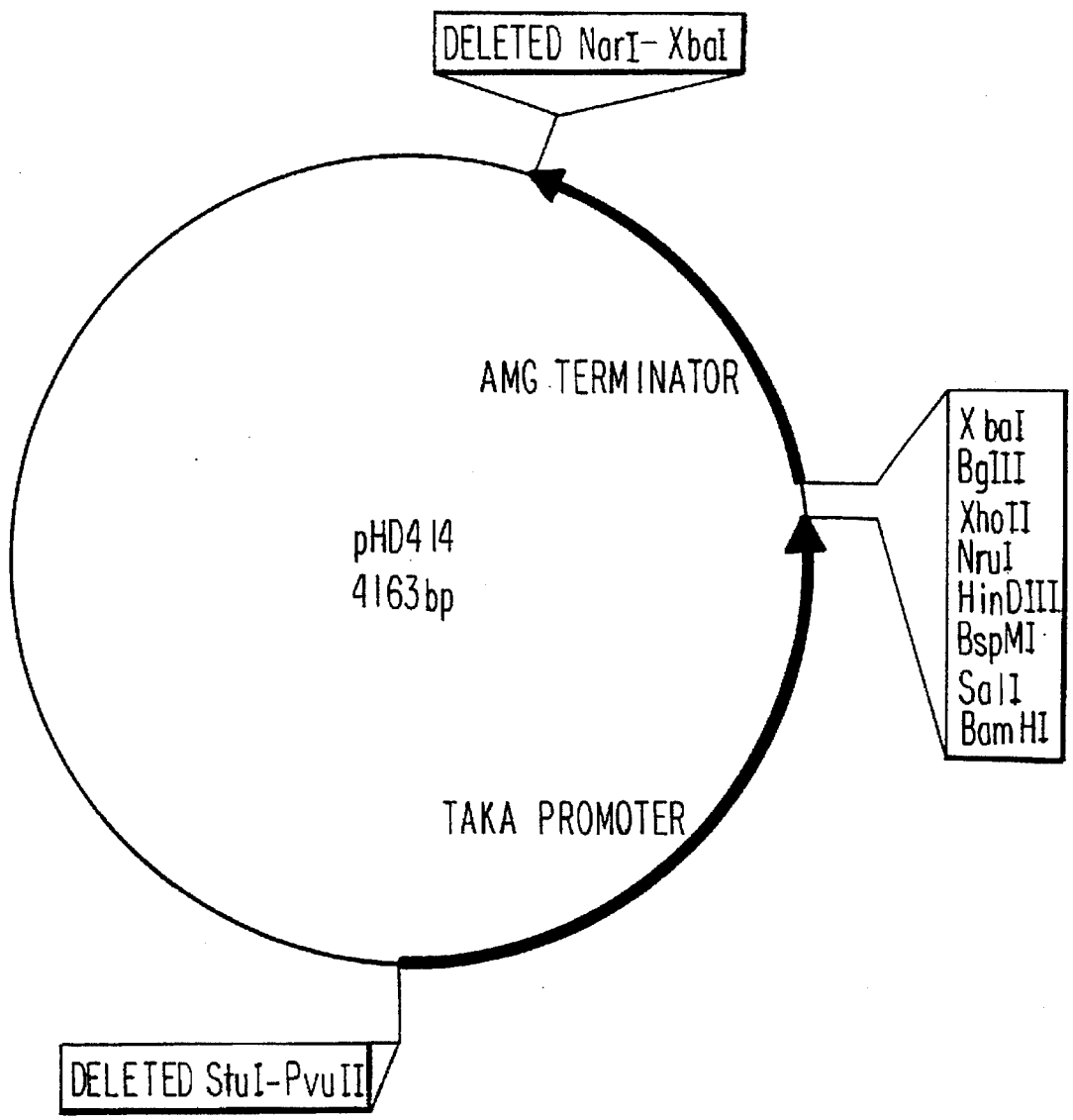

FIG. 11 shows a map of plasmid pHD414, wherein "AMG Terminator" indicates the Aspergillus niger glucoamylase terminator, and "TAKA Promotor" indicates the Aspergillus oryzae TAKA amylase promotor.

In the following it will be explained in detail how the recombinant DNA sequence according to the invention can be produced.

Crude enzyme preparations produced from *Aspergillus aculeatus* for purification of the endo-β-1,4-glucanase can be produced as follows. For the sake of brevity this crude *Aspergillus aculeatus* preparation will be referred to in the following as A.a.e.p.

The strain *Aspergillus aculeatus* CBS 101.43 as a gene donor was fermented in a pilot plant scale in the following way.

An agar substrate with the following composition was prepared in a Fernbach flask:

| | |
|---|---|
| Peptone Difco | 6 g |
| Aminolin Ortana | 4 g |
| Glucose | 1 g |
| Yeast extract Difco | 3 g |
| Meat extract Difco | 1.5 g |
| $KH_2PO_4$ Merck | 20 g |
| Malt extract Evers | 20 g |
| Ion exchanged $H_2O$ | ad 1000 ml | pH was adjusted to between 5.30 and 5.35. Then 40 g of Agar Difco was added, and the mixture was autoclaved for 20 minutes at 120° C. (the substrate is named E-agar).

The strain CBS 101.43 was cultivated on an E-agar slant (37° C.). The spores from the slant were suspended in sterilized skim-milk, and the suspension was lyophilized in vials. The contents of one lyophilized vial was transferred to the Fernbach flask. The flask was then incubated for 13 days at 30° C.

A substrate with the following composition was prepared in a 500 liter seed fermenter:

| | |
|---|---|
| $CaCO_3$ | 1.2 kg |
| Glucose | 7.2 kg |
| Rofec (corn steep liquor dry matter) | 3.6 kg |
| Soy bean oil | 1.2 kg |

Tap water was added to a total volume of around 240 liters. pH was adjusted to around 5.5 before addition of $CaCO_3$. The substrate was sterilized in the seed fermenter for 1 hour at 121° C. Final volume before inoculation was around 300 liters.

The Fernbach flask spore suspension was transferred to the seed fermenter. Seed fermentation conditions were:

Fermenter type: Conventional aerated and agitated fermenter with a height/diameter ratio of around 2.3.

| | |
|---|---|
| Agitation: | 300 rpm (two turbine impellers) |
| Aeration: | 300 normal liter air per minute |
| Temperature: | 30 to 31° C. |
| Time: | around 28 hours |

Around 28 hours after inoculation 150 liters was transferred from the seed fermenter to the main fermenter.

A substrate with the following composition was prepared in a 2500 liter main fermenter:

| | |
|---|---|
| Toasted soy meal | 90 kg |
| $KH_2PO_4$ | 20 kg |
| Pluronic ® antifoam agent | 150 ml |

Tap water was added to a total volume of around 900 liters. The toasted soy meal was suspended in water. pH was adjusted to 8.0 with NaOH, and the temperature was raised to 50° C. Thereafter around 925 Anson units of Alcalase® 0.6 L was added to the suspension. The mixture was held for 4 hours at 50° C. and pH =8.0 ($Na_2CO_3$ addition) with no aeration and 100 rpm agitation. Thereafter the remaining substrate components were added and pH was adjusted to around 6.0 with phosphoric acid. The substrate was sterilized in the main fermenter for 1½ hours at 123° C. Final volume before inoculation was around 1080 liters.

Then 150 liters of seed culture was added.

Fermentation conditions were:

Fermenter type: Conventional aerated and agitated fermenter with a height/diameter ratio of around 2.7.

| | |
|---|---|
| Agitation: | 250 rpm (two turbine impellers) |
| Aeration: | 1200 normal liter air per minute |
| Temperature: | 30° C. |
| Time: | around 151 hours |

From 24 fermentation hours to around 116 fermentation hours pectin solution was added aseptically to the main fermenter at a constant rate of around 8 liters per hour. The pectin solution with the following composition was prepared in a 500 liter dosing tank:

| | |
|---|---|
| Pectin genu*) | 22 kg |
| Phosphoric acid, conc. | 6 kg |
| Pluronic ® antifoam agent | 50 ml |

*)Genu pectin (citrus type NF from the Copenhagen pectin factory Ltd.)

Tap water was added to a total volume of around 325 liters. The substrate was sterilized in the dosing tank for 1 hour at 121° C. Final volume before start of dosage was around 360 liters. When this portion ran out, another similar portion was made. Total volume of pectin solution for one fermentation was around 725 liters.

After around 151 fermentation hours the fermentation process was stopped. The around 1850 liters of culture broth were cooled to around 5° C. and the enzymes were recovered according to the following method.

The culture broth was drum filtered on a vacuum drum filter (Dorr Oliver), which was precoated with Hyflo Super-Cell diatomaceous earth (filter aid). The filtrate was concentrated by evaporation to around 15% of the volume of the culture broth. The concentrate was filtered on a Seitz filter sheet (type supra 100) with 0.25% Hyflo Super-Cell as a filter aid (in the following table referred to as filtration I). The filtrate was precipitated with 561 g of $(NH_4)_2SO_4/l$ at a pH of 5.5, and 4% Hyflo Super-Cell diatomaceous earth is added as a filter aid. The precipitate and the filter aid are separated by filtration on a frame filter. The filter cake is dissolved in water, and insoluble parts are separated by filtration on a frame filter. The filtrate is check filtered on a Seitz filter sheet (type supra 100) with 0.25% Hyflo Super-Cell as a filter aid (in the following table referred to as filtration II). The filtrate is diafiltered on an ultrafiltration apparatus. After diafiltration the liquid is concentrated to a dry matter content of 12.7% (in the following table referred to as dry matter content in concentrate).

A facultative base treatment for partial removal of the protease activity can be carried out at this stage. In case the base treatment is used it is carried out at a pH of 9.2 for 1 hours, whereafter the pH value is adjusted to 5.0.

Now the liquid is check filtered and filtered for the purpose of germ reduction and the filtrate is freeze-dried on a freeze-drying equipment from Stokes.

The pure endo-β-1,4-glucanase is obtainable from the A.a.e.p. as shown in Table 1.

Figure 1:
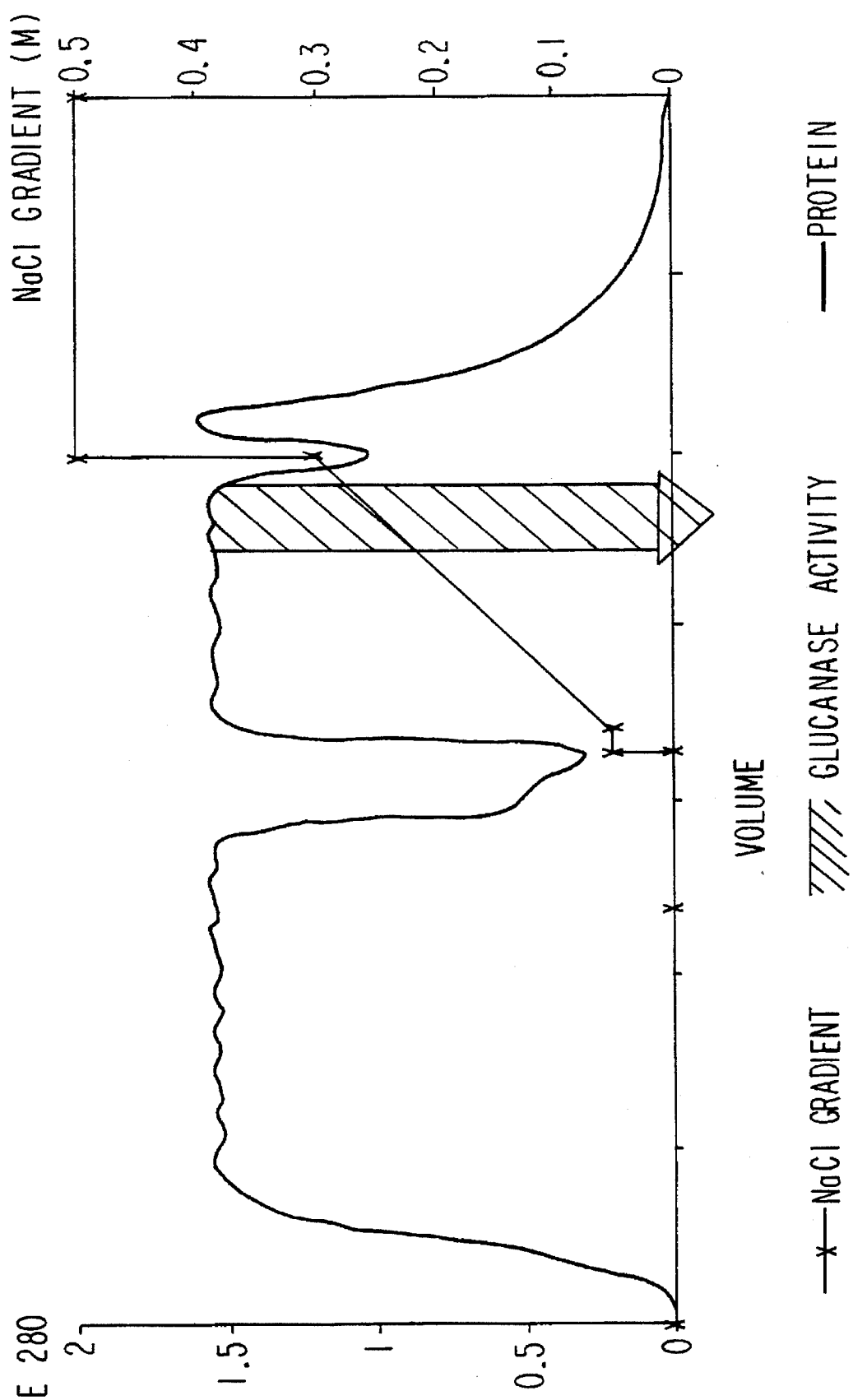
FIG. 1 shows the Ion Exchange Chromatograph (IEC) of the purification of the enzyme of the invention, depicting the endoglucanase fraction pooled from 0.2 m 0.25M NaCl (column: 7.5 * 20 cs, flow=75 ml/minute; clues=20 mM TRIS pH 6.5, increasing NaCl-gradient 0.0 M -step- 0.05M-linear- 0.3M -step- 0.5M)
Figure 2:
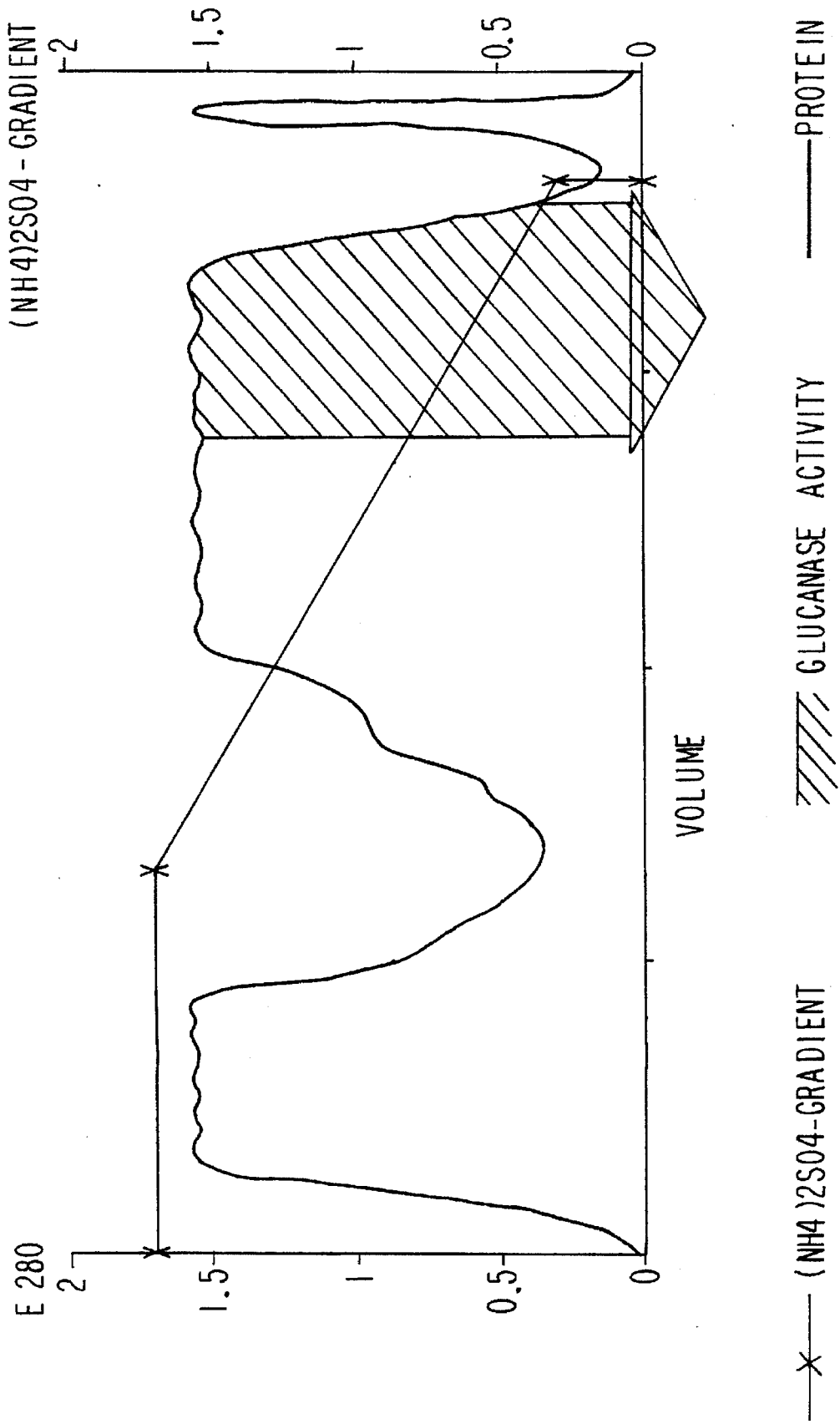
FIG. 2 shows a Hydrophobic Interaction Chromatograph (HIC) of the purification of the enzyme of the invention, depicting the active endoglucanase fraction pooled from 0.9 to 0.4M ammoniumsulfate (column: 5 * 25 cm, flow=50 ml/minute, eluent=water, decreasing ammoniumsulfate-gradient 1.7M -linear- 0.4M-step- 0.0M).

TABLE 1

β-1,4-glucanase purification
*Aspergillus aculeatus* ENZYME BROTH
↓
1: HEAT TREATMENT
60 minutes, 60° C.
↓
2: CENTRIFUGATION
12 500 * g, 30 minutes, supernatant pooled
↓
3: ULTRAFILTRATION
Filtron Minisette, filter area 2800 cm², membrane NMWL 10,000
↓
4: IEC: WATERS ACCELL QMA PLUS; FIG. 1
(column 7.5 * 20 cm, flow 75 ml/minute)
eluent = 20 mM TRIS, pH 6.5, increasing NaCl-gradient
0.0 M-step-0.05 M-linear-0.3 M-step-0.5 M
↓
5: SAMPLE PREPARATION
addition of ammoniumsulfat to 1.7 M concentration
↓
6: HIC: PHENYL-TOYOPEARL 650 (M); FIG. 2
(column: 5 * 25 cm, flow 50 ml/minute)
eluent = water, decreasing ammoniumsulfat-gradient:
1.7 M-linear-0.4 M-step−0.0 M TABLE 1-continued (column 0.8 * 7 cm, flow 2 ml/minute)
eluent = 20 Mm TRIS, pH 6.5, increasing NaCl-gradient:
0.0 M-step-0.1 M-linear-0.15 M-step-0.5 M
↓
ENDO-β-1,4-GLUCANASE
ad 1:
Inactivation and coagulation of heat labile enzyme proteins, other than endo-α-1,4-glucanase
ad 2:
Removal of coagulated proteins
ad 3:
Removal of small particles and about 40% of the colour
ad 4:
IEC is ion exchange chromatography. The endo-β-1,4-glucanase fraction is pooled from step 0.2–0.25 M NaCl
ad 5:
Sample preparation in order to prepare for step 6
ad 6:
HIC is hydrophobic interaction chromatography. The colorless endo-β-1,4-glucanase fraction is pooled from 0.9–0.4 M ammoniumsulfat
ad 7:
Concentration and buffer exchange in order to prepare for step 8
ad 8:
IEC is ion exchange chromatography. Only active endo-β-1,4-glucanase fractions were pooled, which with IEF (isoelectric focusing) and on SDS-PAGE (sodium dodecyl sulfate polyacrylamide gel electrophoresis)/silver show one protein band. The fractions pooled ranged from 0.12–0.14 M NaCl.

The below indicated Table 2 shows how the enrichment factor increases as the purification proceeds.

TABLE 2

| Step | Procedure | Protein (mg) | Enzyme activity (U-units) | Specific activity (U/mg) | Enzyme yield (%) | Enrichment factor |
| --- | --- | --- | --- | --- | --- | --- |
| Initial | crude enzyme | 330 | 24 000 | 0.073 | 100 | 1 |
| 1 | heat treatment | 322 | 23 100 | 0.072 | 96 | 1 |
| 4 | Accell DEAE QMA plus | 6.2 | 17 500 | 2.823 | 73 | 39 |
| 6 | Phenyl Toyopearl 650 (M) | 4.5 | 13 100 | 2.911 | 55 | 40 |
| 8 | Protein Pac DEAE | 2.4 | 10 100 | 4.208 | 42 | 58 |

TABLE 1-continued

Figure 3:
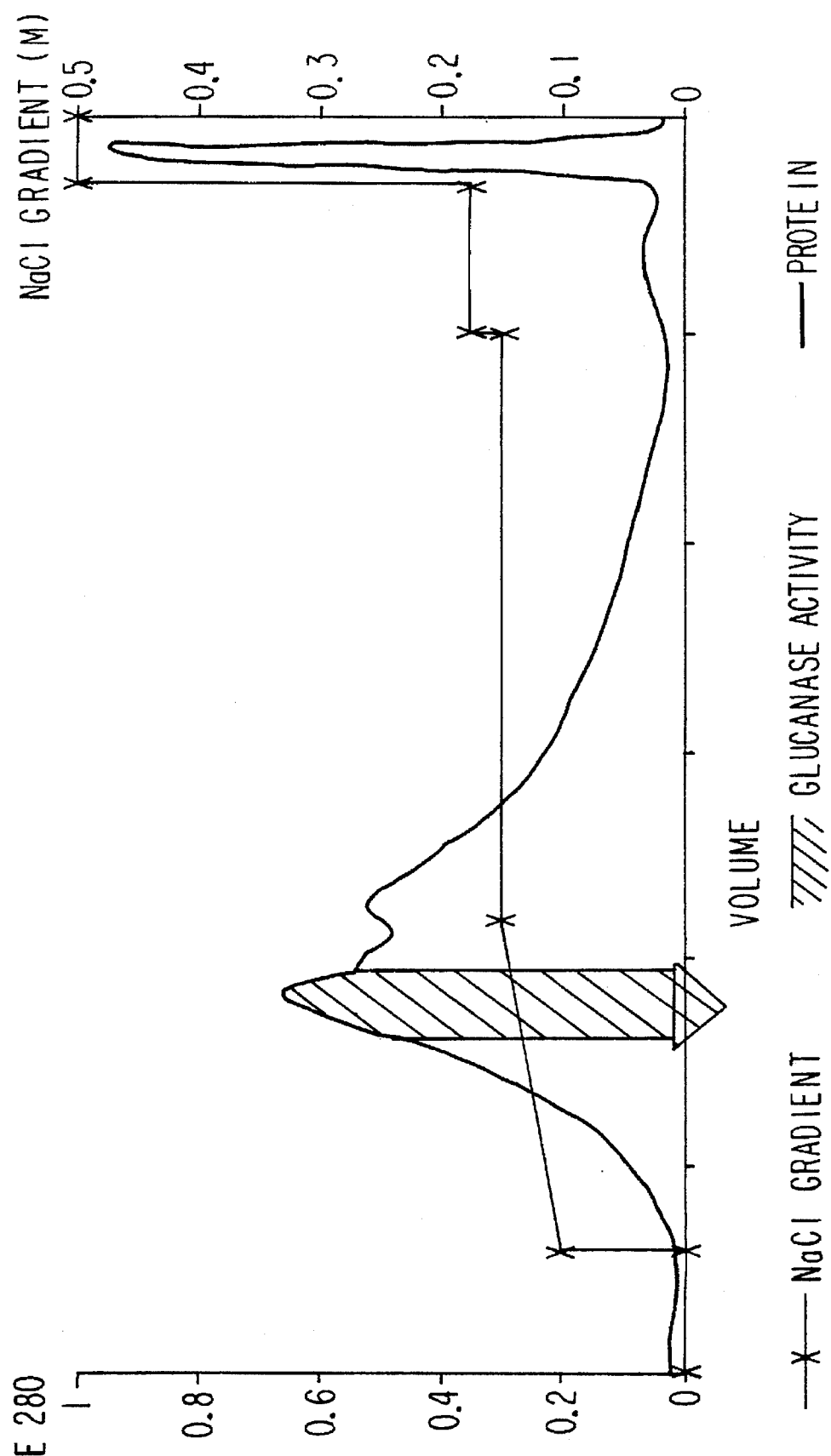
FIG. 3 shows a Ion Exchange Chromatograph (IEC) of the purification of the enzyme of the invention, depicting the active endoglucanase fraction pooled from 0.12 to 0.14M NaCl (column: 0.8 * 7 cm, flow=2 ml/minute, eluent=20 mM TRIS pH 6.5, increasing NaCl-gradient 0.0M-step- 0.1M-linear- 0.15M -step- 0.5M).

↓
7: ULTRAFILTRATION
↓
Filtron Minisette, filter area 2800 cm², membrane NMWL 10,000
↓
8: IEC: PROTEIN PAC DEAE-5-PW; FIG. 3

The thus purified endo-β-1,4-glucanase may be employed for immunization of animals for the production of antibodies. More specifically, antiserum against the endo-β-1,4-glucanase of the invention may be raised by immunizing rabbits (or other rodents) according to the procedure described by N. Axelsen et al. in: *A Manual of Quantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation ($(NH_4)_2SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., Supra, Chapters 3 and 4), or by rocket immunoelectrophoresis (N. Axelsen et al., Chapter 2,).

Unit definition

The U unit indicated in Table 2 is the endo-β-1,4-glucanase activity unit, which is defined as follows: I unit is the amount of enzyme which at 30° C. and in 1 minute degrades carboxymethyl cellulose to reducing carbohydrate corresponding to 1 µmole of glucose.

Amino acid sequence

The following partial amino acid sequence was determined from the purified endo-β-1,4-glucanase by means of automated sequencing (Applied Biosystems 473A protein sequencer)

```
1           5                      (SEQ ID No. 1)
Ala—Ser—Val—Phe—Glu—Trp—Ile—Gly—Ser—
                10
                Asn—Glu—Ser—Gly—Ala—
15
Glu—Phe—Gly—Thr—Ala
```

Thus, a preferred embodiment of the endo-β-1,4-glucanase according to the invention is characterized by the fact that it exhibits the following partial amino acid sequence

```
1           5                      (SEQ ID No. 1)
Ala—Ser—Val—Phe—Glu—Trp—Ile—Gly—Ser—
                10
                Asn—Glu—Ser—Gly—Ala—
15
Glu—Phe—Gly—Thr—Ala
``` or a partial amino acid sequence homologous thereto, this partial amino acid sequence being part of a polypeptide with endo-1,4-β-glucanase activity. Ala no. 1 in the partial sequence is assumed to be the N-terminal amino acid.

In the present context, the term "homologue" is intended to indicate a polypeptide encoded by DNA which hybridizes to the same probe as the DNA coding for the endo-β-1,4-glucanase enzyme under certain specified conditions (such as presoaking in 5×SSC and prehybridizing for 1 h at −40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at −40° C. followed by washing three times in 2×SSC, 0.2% SDS at 40° C. for 30 minutes). More specifically, the term is intended to refer to a DNA sequence which is at least 70% homologous to the sequence shown above encoding the endo-β-1,4-glucanase of the invention. The term is intended to include modifications of the DNA sequence shown above, such as nucleotide substitutions which do not give rise to another amino acid sequence of the endo-β-1,4-glucanase but which correspond to the codon usage of the host organism into which the DNA construct is introduced or nucleotide substitutions which do give rise to a different amino acid sequence and therefore, possibly, a different protein structure which might give rise to an endo-β-1,4-glucanase mutant with different properties than the native enzyme. Other examples of possible modifications are insertion of one or more nucleotides into the sequence, addition of one or more nucleotides at either end of the sequence, or deletion of one or more codons at either end or within the sequence.

The amino acid sequences of the endo-β-1,4-glucanase show no homology with other proteins in the UW-GCG data bank, a publicly available data bank, in relation to which UW is an abbreviation for University of Wisconsin.

The endo-β-1,4-glucanase is further characterized, as indicated in the following.

Figure 4:
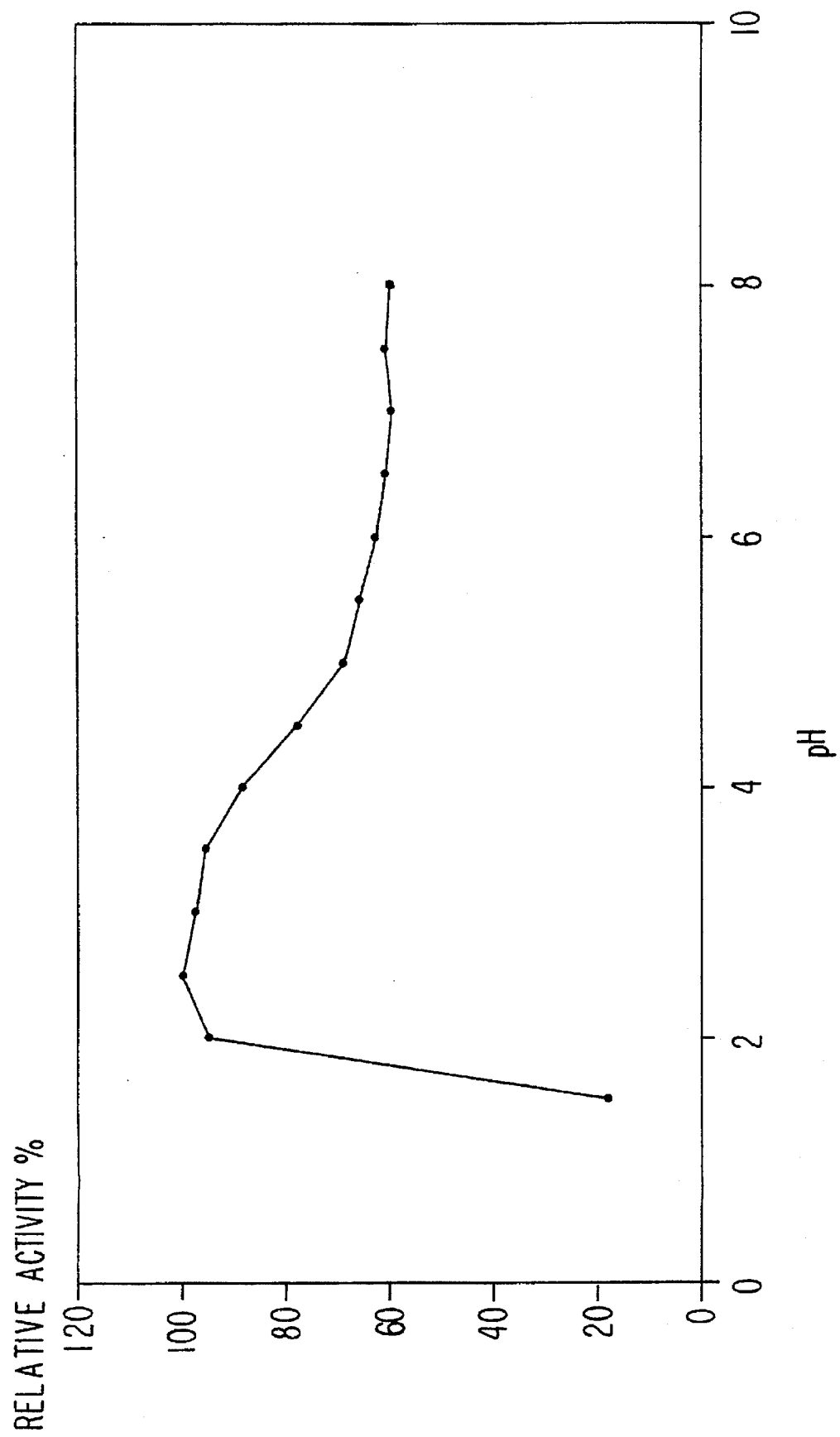
FIG. 4 shows the pH activity (% relative activity) of the endoglucanase of the invention determined in the range of pH 1.5 to pH 8.
Figure 5:
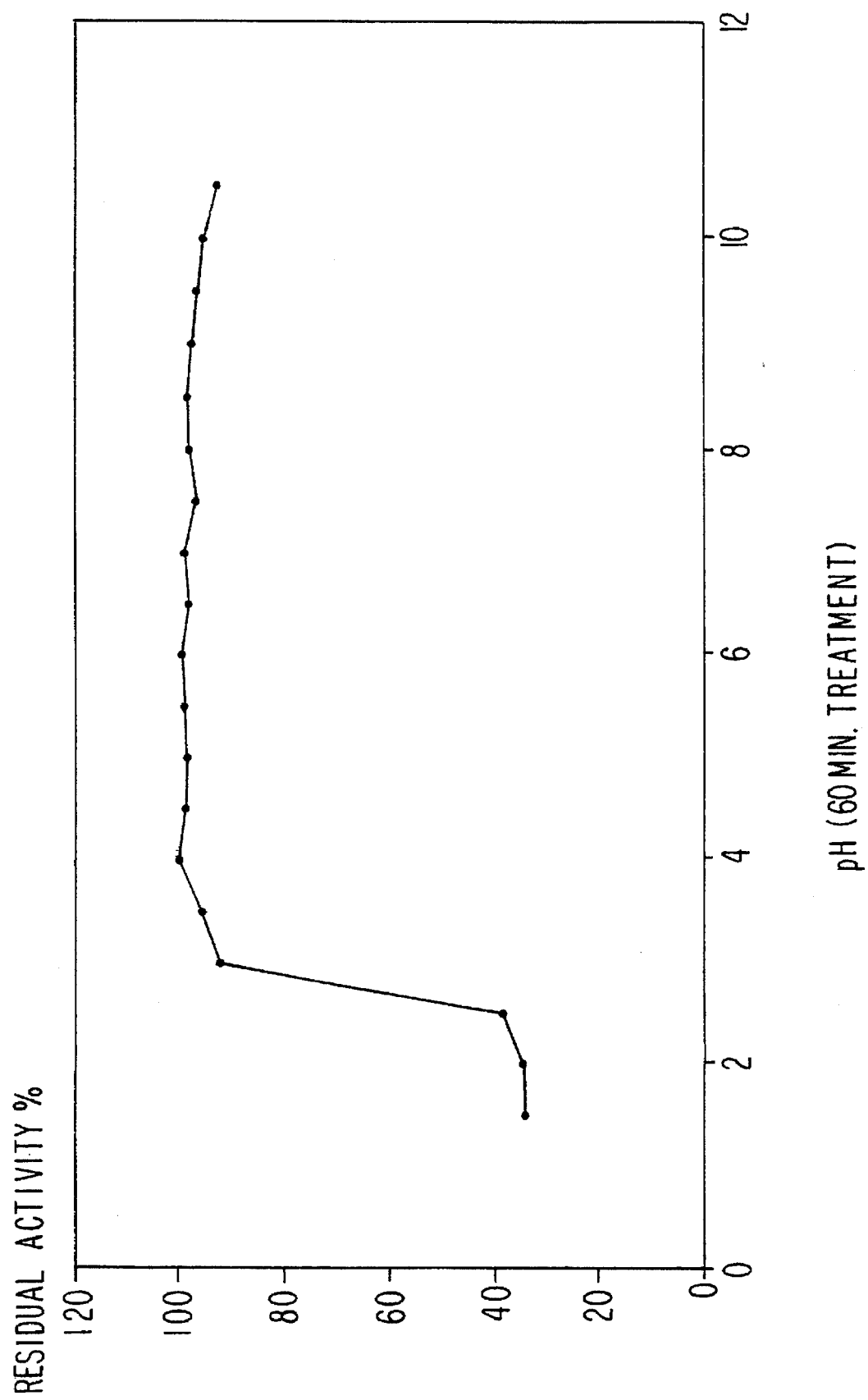
FIG. 5 shows the pH stability (% residual activity) of the endoglucanase of the invention determined after 60 minutes of incubation at a pH in the range of pH 1.5 to pH 1.1.

FIGS. 4 and 5 show the pH activity and pH stability, respectively, of the endo-β-1,4-glucanase.

This endo-β-1,4-glucanase has its pH optimum at pH 2.5. The main activity ($\geq 80\%$) ranges between pH 2–4.

The pH stability of the endo-β-1,4-glucanase is good between pH 3 and $\geq 10.5$, when treated for 1 hour at room temperature. The enzyme is not stable at pH below 3.

Figure 6:
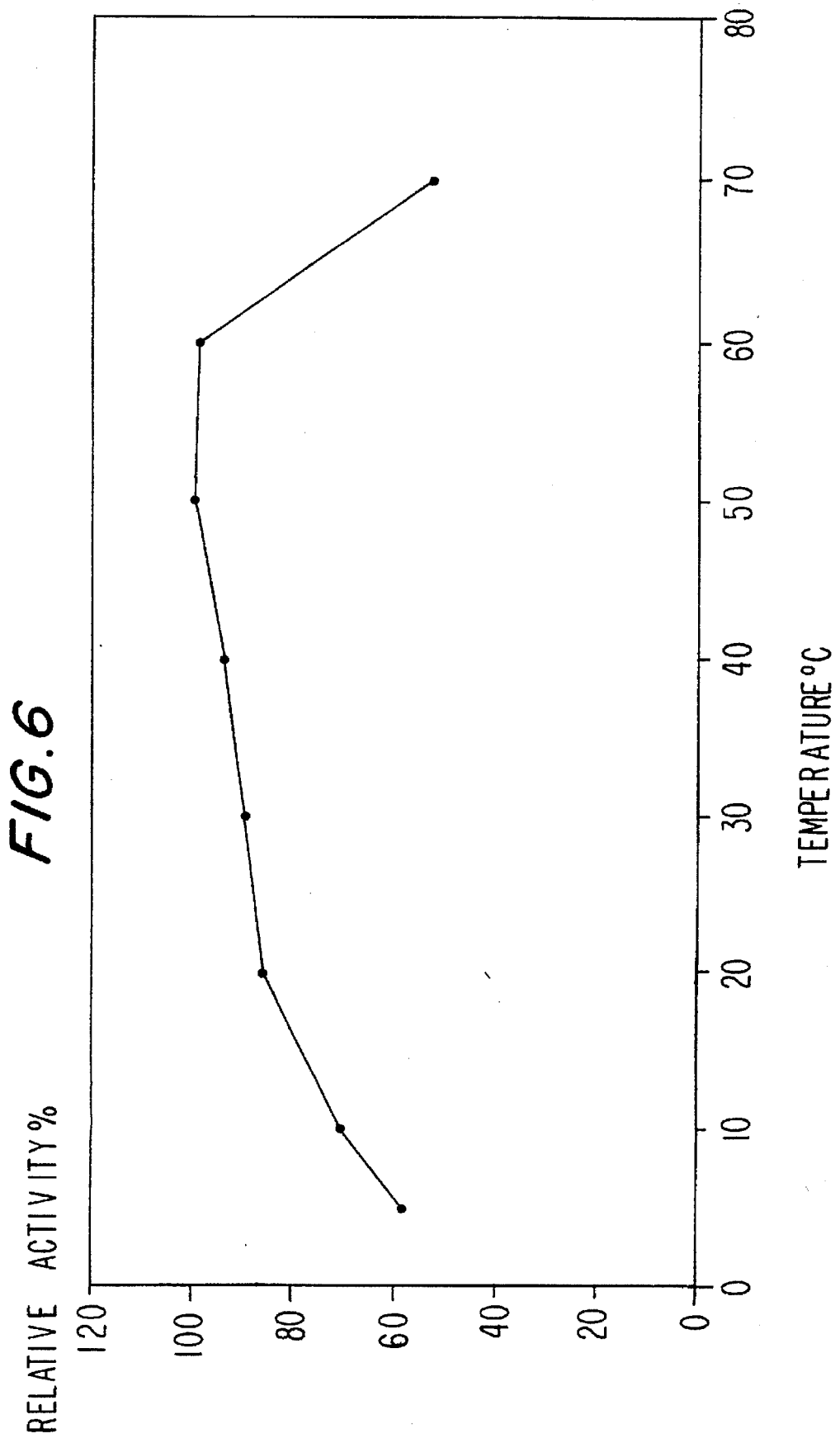
FIG. 6 shows the temperature activity (% relative activity) of the endoglucanase of the invention determined in the range of 5° to 70° C.
Figure 7:
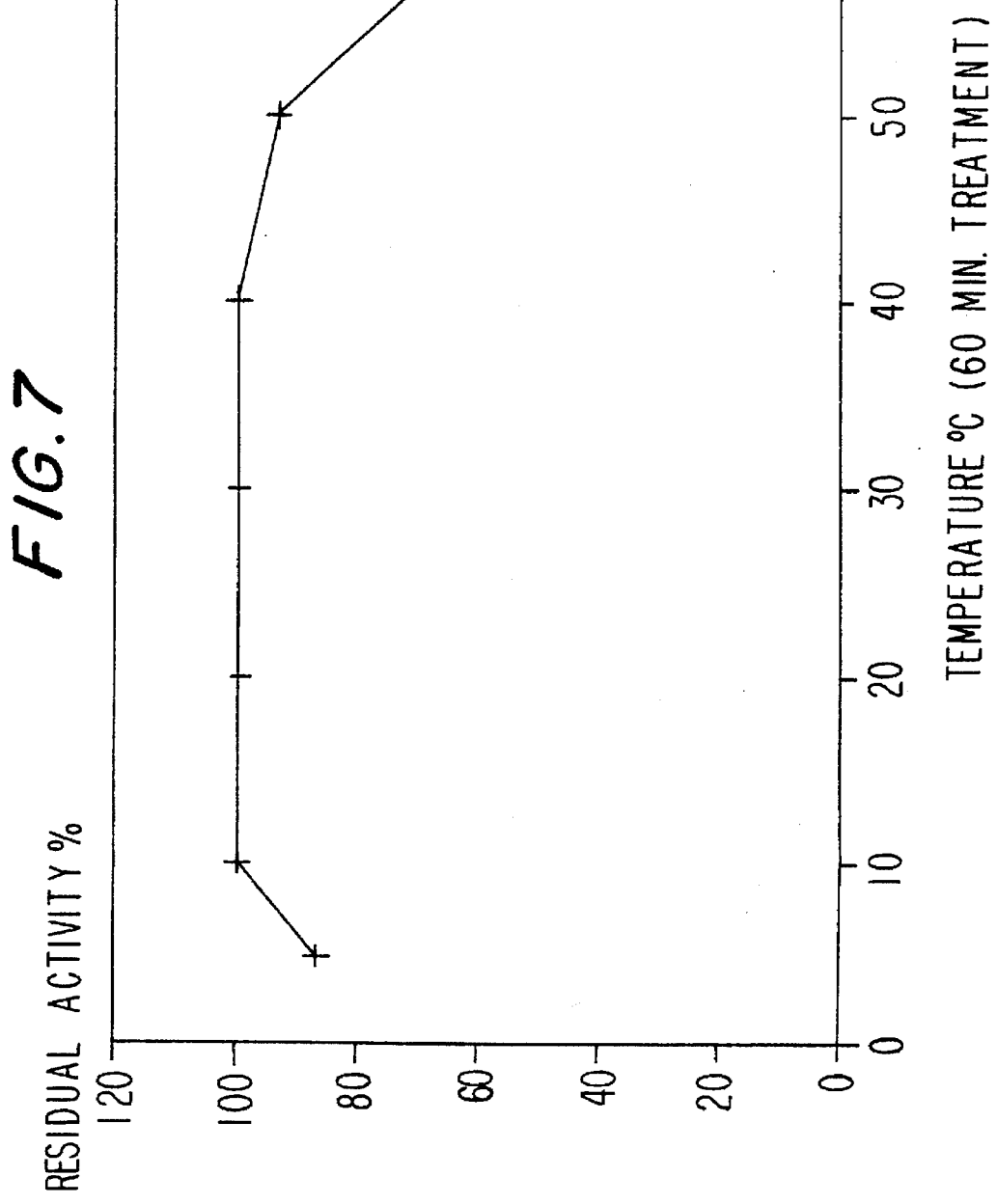
FIG. 7 shows temperature stability (% residual activity) of the endoglucanase of the invention determined after 60 minutes of incubation in the range of 50° to 70° C.

FIGS. 6 and 7 show the temperature activity dependency and the temperature stability dependency, respectively, of the endo-β-1,4-glucanase.

The temperature optimum of the endo-β-1,4-glucanase is around 50°–60° C., and the temperature activity range is relatively broad:

$\geq 80\%$ activity in the range of 20°–65° C.

$\geq 50\%$ activity in the range of 5°–70° C.

This activity of the endo-β-1,4-glucanase in the more acidic range (pH 2–4), together with the broad temperature profile, especially at lower temperatures (5°–20° C.) makes this enzyme especially suitable for the wine and juice area.

In the temperature range of 5°–50° C. the endo-β-1,4-glucanase activity is not remarkably influenced after a treatment of 1 hour at pH 4.5 ($\geq 80\%$ of the initial activity).

Molecular weight: 38.000 Dalton

Isoelectric point: pH<2.8

Figure 8:
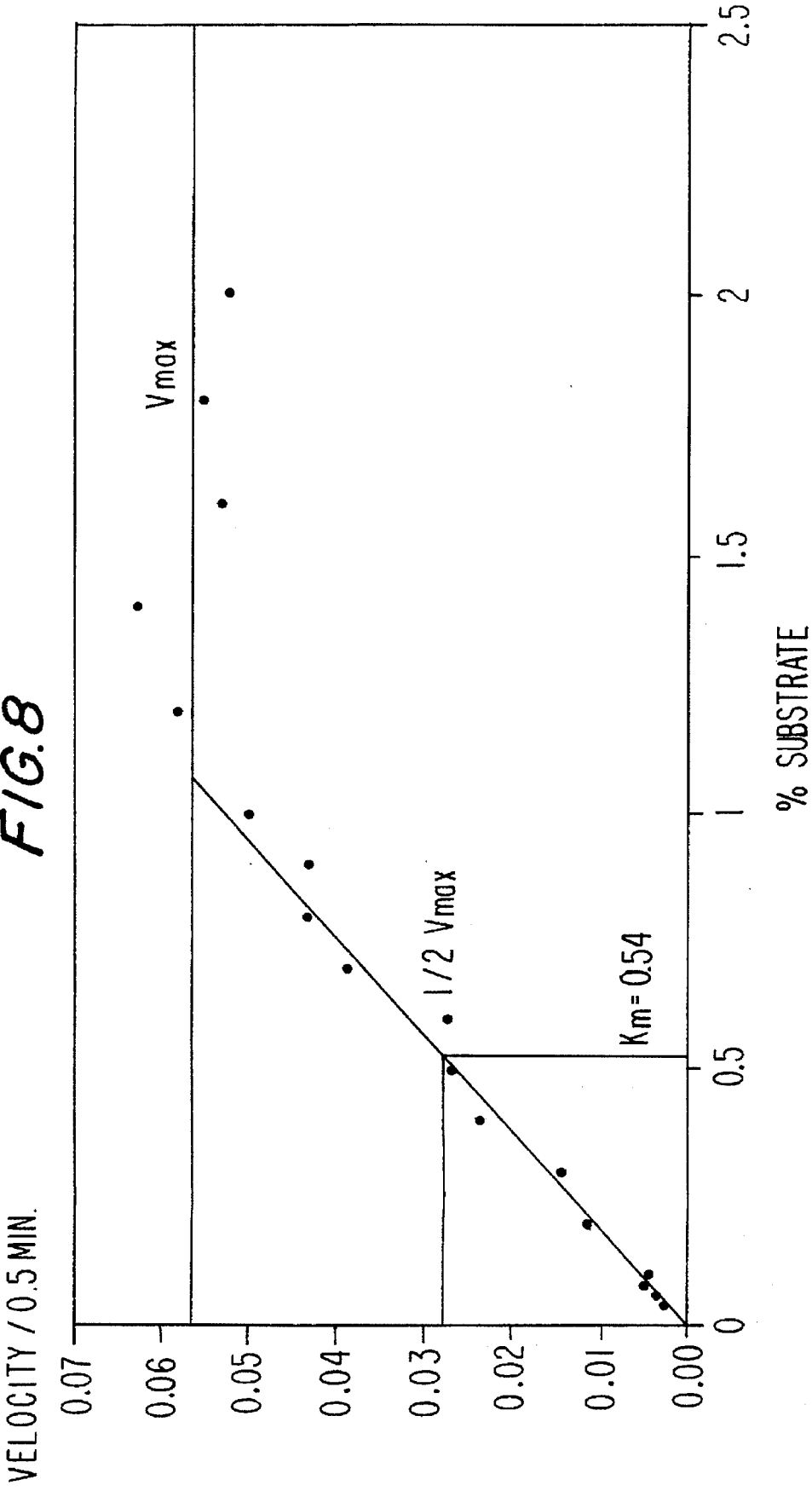
FIG. 8 shows a graphic presentation of the kinetics of the enzyme of the invention from which Vmax and Km are calculated.
Figure 9:
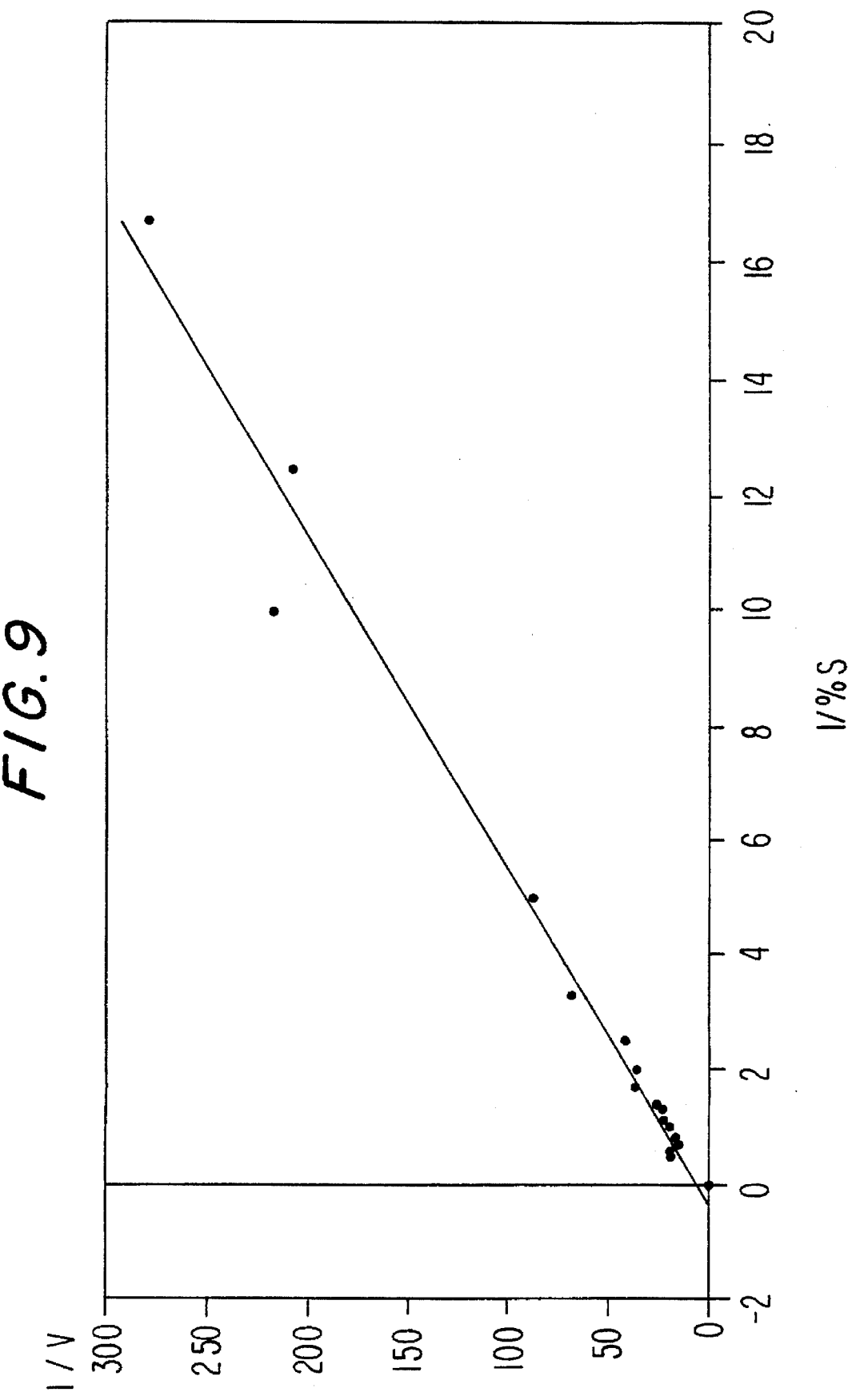
FIG. 9 shows a graphic presentation (Lineweaver-Bark plot) of the kinetics of the enzyme of the invention.

Km-value: The Michaelis-Menten-Kinetic and the corresponding Lineweaver-Burk-kinetic appears from FIGS. 8 and 9, respectively. The resulting Km-value is expressed in %-substrate concentration (not in mole/l, the reason for this being the inhomogenity of the molecular weight distribution of the substrate; therefore it was not possible to calculate an accurate figure for the molecular weight).

The theoretical and calculated Km-value is

Km=0.54% carboxymethyl cellulose (SERVA 16110)

A preferred embodiment of the endo-β-1,4-glucanase according to the invention is characterized by the fact that the endo-β-1,4-glucanase exhibits a pH-optimum of 2.0–4.0, preferably 2.5–3.3, an isoelectric point of 2.0–3.5, preferably 2.5–3.1, a molecular weight of between 30,000 and 50,000, preferably 35,000 and 45,000, and a temperature optimum between 30° and 70° C., preferably between 40° and 65° C.

Also the invention comprises a recombinant DNA sequence, which is characterized by encoding for the endo-β-1,4-glucanase according to the invention.

A preferred embodiment of the recombinant DNA sequence according to the invention is characterized by the fact that it comprises at least one of the following partial DNA sequences a) CAGTCGACAG GCACCATGAA GCTGCTTAAC CTACTTGTTG CTGCTGCCGC GGCCGGCAGT (SEQ ID No. 2)

b) GCAGTGGCGG CCCCGACCCA CGAACACACG AAGCGGGCTT CTGTTTTCGA ATGGATCGGA (SEQ ID No. 3)

c) TCCAATGAGT CGGGCGCCGA GTTCGGCACC GCATTCGGAA CTTGGGGTAT CGACT (SEQ ID No. 4)

A preferred embodiment of the recombinant DNA sequence according to the invention is characterized by the fact that it comprises the following partial DNA sequence

---

CAGTCGACAG GCACCATGAA GCTGCTTAAC CTACTTGTTG CTGCTGCCGC
GGCCGGCAGT GCAGTGGCGG CCCCGACCCA CGAACACACG AAGCGGGCTT
CTGTTTTCGA ATGGATCGGA TCCAATGAGT CGGGCGCCGA GTTCGGCACC
GCATTCGGAA CTTGGGGTAT CGACT (SEQ ID No. 5)

---

A preferred embodiment of the recombinant DNA sequence according to the invention is characterized by the fact that it comprises a DNA sequence selected from a) The *Aspergillus aculeatus* endo-β-1,4-glucanase DNA insert in pHD446 b) a DNA sequence which hybridizes to the coding region for the mature endo-β-1,4-glucanase DNA comprised by the DNA insert of a) and which comprises a structural gene for a polypeptide with endo-β-1,4-glucanase activity, and optionally a promoter, a coding region for a signal or leader peptide and/or transcriptional terminator.

c) a DNA sequence with a homology sufficient to hybridize to one of the sequences indicated in claim 3 under relative stringent conditions (1.0×SSC, 0.1% SDS, 65° C.), reference being made to T. Maniatis, A laboratory Manual (CSH)

d) a derivative of a DNA sequence defined in a), b) or c), or e) a DNA sequence which codes for a mature endo-β-1, 4-glucanase or a signal peptide or a leader peptide thereof and which is degenerate within the meaning of the genetic code with respect to a DNA sequence of a), b) or c).

Also, the invention comprises a vector which is characterized by the fact that it comprises the recombinant DNA sequence according to the invention.

A preferred embodiment of the vector according to the invention is characterized by the fact that the promoter is the *Aspergillus oryzae* takaamylase promoter.

Also the invention comprises a transformed host which is characterized by the fact that it contains the vector according to the invention.

A preferred embodiment of the transformed host according to the invention is characterized by the fact that the transformed host is an *Aspergillus* strain. Hereby a good production capacity of the endo-β-1,4-glucanase is obtained.

A preferred embodiment of the transformed host according to the invention is characterized by the fact that the transformed host is a strain belonging to the species *Aspergillus aculeatus, Aspergillus niger, Aspergillus oryzae* or *Aspergillus awamori*. Hereby a good production capacity of the endo-β-1,4-glucanase is obtained.

A preferred embodiment of the transformed host according to the invention is characterized by the fact that the transformed host is a microorganism, which in its non-transformed condition does not produce endo-β-1,4-glucanase or only produces endo-β-1,4-glucanase in insignificant amounts, preferably Bacillus sp., *E. coli* or *S. cerevisiae*. Hereby a "tailor made" enzyme preparation with high endo-β-1,4-glucanase activity and a spectrum of other wanted specific enzyme activities can be obtained.

Also, the invention comprises a method for production of a endo-β-1,4-glucanase by use of a transformed host according to the invention. By means of this method the endo-β-1,4-glucanase can be obtained in high yield.

Also, the invention comprises the endo-β-1,4-glucanase, when produced by the method according to the invention. The endo-β-1,4-glucanase can be obtained in high yield.

Also, the invention comprises an enzyme preparation which is characterized by the fact that it contains a pectinase preparation usable for degradation or modification of plant cell walls enriched with the endo-β-1,4-glucanase according to the invention, preferably with an enrichment factor of at least 1.1. In this manner a boosting of the cell wall degrading ability of the pectinase preparation can be obtained.

A preferred embodiment of the enzyme preparation according to the invention is characterized by the fact that the pectinase preparation is producible by means of a microorganism belonging to the genus Aspergillus, preferably *Aspergillus niger, Aspergillus aculeatus, Aspergillus awamori* or *Aspergillus oryzae*. Such preparation is able to provide an extraordinary good total liquefaction power and thus a marked viscosity decrease of apple mash and similar biological materials. This will be documented in a later part of the specification in case the pectinase preparation is A.a.e.p.

A preferred embodiment of the enzyme preparation according to the invention is characterized by the fact that the endo-β-1,4-glucanase is the endo-β-1,4-glucanase produced by means of the method according to the invention. The production costs of this preparation are relatively low.

Also, the invention comprises a use of the endo-β-1,4-glucanase according to the invention as an agent for degradation or modification of celluloses.

A preferred embodiment of the use of the endo-β-1,4-glucanase according to the invention is a use as an agent for degradation or modification of plant cell walls. At present, degradation of plant cell walls is the most preferred use of the endo-β-1,4-glucanase according to the invention, due to the high plant cell wall degradation activity.

Also the invention comprises a use of the enzyme preparation according to the invention as an agent for degradation or modification of celluloses.

A preferred embodiment of the use of the enzyme preparation according to the invention is a use as an agent for degradation or modification of plant cell walls. At present, degradation of plant cell walls is the most preferred use of the enzyme preparation according to the invention, due to the high plant cell wall degradation activity.

FIG. 10 is a map of plasmid pYHD17, wherein "TPI promoter" indicates the *S. cerevisiae* triose phosphate isomerase promoter, "Terminator" indicates the transcription terminator, "Amp" indicates the gene mediating ampicillin resistance, "2μ ori" indicates the yeast plasmid 2μ origin of replication, and "URA3" indicates a gene encoding a selection marker complementing a uracil deficiency in the host strain.

Construction of an expression plasmid

The commercially available plasmid pYES II (Invitrogen) was cut with SpeI, filled in with Klenow DNA polymerase+ dNTP and cut with ClaI. The DNA was size fractionated on an agarose gel, and a fragment of about 2000 bp was purified by electroelution. The same plasmid was cut with ClaI/PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from S. cerevisiae (cf. T. Albers and G. Kawasaki, J. Mol. Appl. Genet. 1.1982, pp. 419–434) was slightly modified: an internal SphI site was removed by deleting the four bp constituting the core of this site. Furthermore, redundant sequences upstream of the promoter were removed by BalI exonuclease treatment followed by addition of a SphI linker. Finally, an EcoRI linker was added at position −10. After these modifications, the promoter is included in a SphI-EcoRI fragment. Its effeciency compared to the original promoter appears to be unaffected by the modifications. The resulting plasmid pYHD17 is shown in FIG. 10.

Donor organism mRNA was isolated from Aspergillus aculeatus CBS 101.43 grown in a soya-rich fermentation medium with agitation to ensure sufficient aeration.

Isolation of mRNA

Total RNA was isolated from approximately 7 g of mycelium. The mycelium was frozen in liquid nitrogen and ground in a mortar with 1 g of quartz sand to a consistency of flour. The RNA was extracted with guanidinium thiocyanate and centrifuged through CsCl essentially as described in Sambrook et al., 1989, op. cit.. Poly A RNA was isolated from total RNA by chromatrography on oligo dT cellulose.

cDNA synthesis cDNA synthesis was carried out by means of a cDNA synthesis kit from Invitrogen according to the manufacturer's specifications. The DNA was adapted to the expression vectors by addition of a BstxI linker (invitrogen) and size fractionated on an agarose gel. Only DNA larger than 5–600 bp was used in the library construction. The adapted cDNA was ligated into an appropriate vector cut with BstxI. Following test ligations (in order to determine the size of the library) the library was plated onto 50 agar plates. To each plate containing from approximately 500 to 5000 individual clones (dependent on the library size) was added 3 ml medium. The bacteria were scraped off, 1 ml glycerol was added, and stored at −80° C. as 50 pools. The remaining 2 ml were used for DNA isolation. If the amount of DNA was insufficient to give the required number of yeast transformants (see below), large scale DNA was prepared from 500ml medium (TB) inoculated with 50 μl −80° C. bacterial stock propagated over night.

Construction of Yeast Libraries

DNA from one or more pools was transformed into yeast as described below. To ensure that all the bacterial clones were tested in yeast a number of yeast transformants 5× larger than the number of bacteria clones in the original pools was set as a limit.

Transformation of yeast

The yeast strain used was yNG231. (MAT alpha, leu2, ura3-52, his4-539, pep4-delta 1, cir+). One colony was grown at 30° C. overnight in 10 ml YPD (this culture can be stored for several days at 5° C.).

10, 30, and 60 μl of this culture were added to 3 shaker flasks containing 100 ml YPD, and incubated with shaking overnight at 30° C. The culture with an $OD_{600}$ closest to 0.3–0.4 was selected. The cells were harvested in 50 ml tubes in a Beckman centrifuge (speed 6, 10 minutes), the cells were resuspended in 2×5 ml $H_2O$, centrifuged as described above, resuspended in 5 ml buffer containing 0.1M LiAc, 10 mM Tris-Cl, 1 mM EDTA, pH 7.5, and centrifuged again. The cells were resuspended in 500 μl of the above buffer and incubated for 60 minutes at 30° C. 250 μg carrier DNA (sterile salmon-sperm DNA 10 mg/ml) was added and aliquots of 100 μl were prepared. The DNA to be transformed (approx. 5 μg) was added to the 100 μl aliquot, mixed gently, and incubated for 30 minutes at 30° C. 700 μl 40% PEG 4000, 0.1M LiAc, 10 mM Tris-Cl, 1 mM EDTA, pH 7.5 was added, and incubation was continued for 60 minutes at 30° C. The transformation mixture was subjected to heat shock for 5 minutes at 42° C., spun briefly in a micro centrifuge, resuspended in 100–200 μl $H_2O$, and plated on SC plates without uracil, followed by incubation for three days at 30° C.

Preparation of carrier DNA 100 mg salmon-sperm DNA was weighed out and dissolved overnight in 10 ml 10 mM Tris-CI, 1 mM EDTA, pH 7,5 (TE). The solution was then sonicated in a plastic container in ice water until it was no longer viscous. The solution was then phenole extracted and EtOH precipitated, and the pellet was washed and resuspended in 5 ml TE. The suspension was EtOH precipitated, and the pellet was washed and resuspend in 5 ml TE. The $OD_{260}$ was measured, and the suspension was diluted with TE to 10 mg/ml.

Transformation of Aspergillus oryzae or Aspergillus niger (general procedure)

100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6M $MgSO_4$. The mycelium is suspended in 15 ml of 1.2M $MgSO_4$. 10 mM $NaH_2PO_4$, pH =5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH=7.0. Centrifugation is performed for 15 minutes at 100 g and the protoplasts are collected from the top of the $MgSO_4$ cushion. 2 volumes of STC (1.2 M sorbitol, 10 mM Tris-HCl, pH=7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 μl of protoplast suspension is mixed with 5–25 μg of the appropriate DNA in 10 μl of STC. Protoplasts are mixed with p3SR2 (an A. nidulans amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove Biochem. Biophys. Acta 113 (1966) 51–56) containing 1.0M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Construction of an Aspergillus expression vector

The vector pHD414 (FIG. 11) is a derivative of the plasmid p775 (described in EP 238 023). In contrast to this plasmid, pHD414 has a string of unique restriction sites between the promoter and the terminator. The plasmid was constructed by removal of an approximately 200 bp long fragment (containing undesirable RE sites) at the 3'end of the terminator, and subsequent removal of an approximately 250 bp long fragment at the 5'end of the promoter, also containing undesirable sites. The 200 bp region was removed by cleavage with NarI (positioned in the pUG vector) and XbaI (just 3' to the terminator), subsequent filling in the generated ends with Klenow DNA polymerase +dNTP, purification of the vector fragment on gel and religation of the vector fragment. This plasmid was called pHD41 3. pHD41 3 was cut with StuI (positioned in the 5'end of the promoter) and PvuII (in the pUC vector), fractionated on gel and religated, resulting in pHD41 4. FIG. 11 is a map of plasmid pHD41 4, wherein "AMG Terminator" indicates the A. niger glucoamylase terminator, and "TAKA Promoter" indicates the A. oryzae TAKA amylase promoter.

Analytical methods

The fermentation broths are analyzed by vibration viscosimetry on CMC at pH 6.0. The method is described in AF 275/1 which is obtainable on request from Novo Nordisk A/S. The unit designation is EGU.

Media

YPD: 10 g yeast extract, 20 g peptone, $H_2O$ to 810 mi. Autoctaved, 90 ml 20% glucose (sterile filtered) added.

YPG-agar: 25 g/l Bactoagar, 15 g/l glucose, 5 g/l $K_2PO_4$, 0.5 g/l $MgSO_4$—$7H_2O$, pH adjusted to 5.0. Autoclaved.

10× Basal salt: 66.8 g yeast nitrogen base, 100 g succinic acid, 60 g NaOH, $H_2O$ ad 1000 ml, sterile filtered.

SC-URA: 90 ml 10× Basal salt, 22.5 ml 20% casamino acids 9 ml 1% tryptophane, $H_2O$ ad 806 ml, autoclaved, 3.6 ml 5% threonine and 90 ml 20% glucose added.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

CMC overlayer gel: 1% agarose, 1% carboxymethyl cellulose (CMC) (7LFD) in 0,1M citrate-phosphate buffer, pH 4.5. The get was boiled and then cooled to 55° C. before the overlayer was poured onto agar plates.

FG-4-Agar: 35 g/l agar, 30 g/l Soy bean meal, 15 g/l maltodextrin (Glucidex 6), 5 g/l Bacto pepton, pH 7. Autoclaved 40 min at 121° C.

FG-4 medium: 30 g/l Soy bean meal, 15 g/l maltodextrin (Glucidex 6), 5 g/l Bacto pepton. Autoclaved 40 min at 121° C.

EXAMPLE 1

A library from *Aspergillus aculeatus* CBS 101.43 consisting of approx. 300,000 individual clones in 50 pools was constructed in *E. coli* as previously described.

DNA was isolated from 20 individual clones from the library and subjected to analysis for cDNA insertion. The insertion frequency was found to be >90% and the average insert size was approximately 1400 bp.

DNA from the *Aspergillus aculeatus* library, was transformed into yeast, and plates containing 20–30,000 colonies were obtained from each pool. The colonies were scraped off and stored in glycerol at −80° C.

Yeast cells from the library were spread onto YNB agar to a total of about 250,000 colonies. The number of colonies per plate varied from 50 to 500. After 4 or 5 days of growth, the agar plates were replica plated onto two sets of SC-H agar plates. These plates were then incubated for 2–4 days at 30° C. before the two sets of agar plates were overlayered with an CMC overlayer gel for detection of endo-β-1,4-glucanase activity. After incubation overnight at 40° C., enzyme reactions were visualised with Congo Red. First 10–15 ml 0,5M tris-borate buffer pH 8.4 was poured onto the plates and removed after approx. 30 min. The 10–15 ml of a 0.5% solution of Congo Red was poured onto the overlayer and removed after 10–20 min. The plates were then washed once or twice by pouring 10–15 ml of 2M NaCl onto the plates. The NaCl solution was removed after 15–25 min. Endo-β-1,4-glucanase positive colonies were identified as colonies with colourless or pale red clearing zones on a red background.

Cells from enzyme-positive colonies were spread for single colony isolation on agar, and an enzyme-producing single colony was identified and selected by the above described overlayer method.

Endo-β-1,4-glucanase positive yeast isolates were identitified and confirmed positive.

EXAMPLE 2

Isolation of DNA

An isolate was inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol. 100 μl 2 mg/ml Zymolase was added, and the suspension was incubated at 37° C. for 30 minutes and spun for 30 seconds. The pellet (spheroplasts) was resuspended in 0.4 ml TE. 90 μl of (1.5 ml 0.5 M EDTA pH 8.0, 0.6 ml 2M Tris-Cl pH 8.0, 0.6 ml 10% SDS) was added, and the suspension was incubated at 65° C. for 30 minutes. 80 μl 5M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% EtOH, spun for 30 seconds and dried at room temperature. The pellet was resuspended in 50 μl TE (Tris-EDTA) and spun for 15 minutes. The supernatant was transferred to a fresh tube. 2.5 μl 10 mg/ml RNase was added, followed by incubation at 37° C. for 30 minutes and addition of 500 μl isopropanol with gentle mixing. The mixture was spun for 30 seconds, and the supernatant was removed. The pellet was rinsed with cold 96% EtOH and dried at room temperature. The DNA was dissolved in 50 μl water to a final concentration of approximately 100 μl/ml.

The DNA was transformed into *E. coli.* by standard procedures. Two *E. coli* colonies were isolated and analysed with the restriction enzymes HindIII and XbaI which excised the DNA insert.

Some partial DNA sequences of the positive clone were determined, vide claim 4. The clone was found to encode a protein with an N-terminal amino acid sequence identical to the N-terminal on the purified β-glucanase.

EXAMPLE 3

Expression of glucanase

In order to express the glucanase the DNA was digested with HindIII/XbaI, size fractionated on gel, and a fragment corresponding to the glucanase gene was purified. The gene was subsequently ligated to HindIII/XbaI digested pHD414 resulting in the plasmid pHD446.

After amplification of the DNA in *E. coli* the plasmid pHD446 was transformed into Aspergillus oryzae as described above.

Test of *Aspergillus oryzae* transformants

Each of 13 transformants were inoculated in the center of a Petri dish with FG-4 agar. After 5 days of incubation at 30° C. 4 mm diameter plugs were removed from the center of the colonies by a cork borer. The plugs were imbedded in CMC overlayer gel, and incubated overnight at 40° C. The glucanase activity was visualized by Congo Red as described above. The best transformant had a clearing zone at 19 mm and thereby demonstrates higher glucanase activity than the *Aspergillus oryzae* background which generated clearing zones of 0–5 mm. This demonstrates efficient expression of endo-β-1,4-glucanase in *Aspergillus oryzae*. The best transformant was selected and inoculated and maintained on YPG-agar.

The transformant was inoculated from YPG-agar slants on 500 ml shake flask with FG-4. After 4 days of fermentation with sufficient agitation to ensure good aeration, the culture broths were centrifuged for 10 minutes at 2000 g and the supernatants were analyzed. The activity was 8 EGU/ml.

Pectin extraction

Pectins have gelation and stabilisation properties, which make them useful for the food industry. They are commercially extracted from waste materials of the food industry, e.g. citrus peels, apple pomace or sugar-beet pulp.

Most often the extraction with acids (sulphuric acid or nitric acid) is used for the production of pectins. At a pH around 2 and at an elevated temperature the pectins are extracted from plant material and precipitated with alcohol after precipitation.

This acid extraction has several disadvantages: water pollution, corrosion, filtering problems due to desintegration of the plant cell walls, partial break down of the wanted pectin polymers (the degree of polymerisation is one of the most important parameters of a commercial pectin). Thus, it is obvious, that an extraction of pectins with enzymes, which do not decompose native pectin polymers would be of great advantage.

Industrial apple pomace for the pectin production was used to compare the amount of pectin extractable either by chemicals or endo-β-1,4-glucanase.

Chemical extraction of pectin (prior art)

To 1 part of pomace 19 parts of distilled water was added and the mixture was heated to the boiling point in order to bring the soluble part of the pomace into solution. The pH value was adjusted to 1.9 by means of 2N $H_2SO_4$. The mixture is held at this pH for 2.5 hours at 90° C. and afterwards cooled to room temperature. The mixture is filtered and the pomace residues washed with 10 parts of distilled water.

To 1 part of the filtrate 6 parts of methanol is added. After 30 minutes standing the mixture is filtered and pressed. The alcohol insoluble substance (AIS) is washed with 4 parts of methanol and filtered and pressed again.

The obtained AIS is dried at 60° C. for one hours.

From this AIS the amount of starch is determined with the test kit from Boehringer Mannheim (order no. 207748).

The amount of obtained pectin is calculated by determination of the amount of AIS in % obtained from the dry matter substance from the pomace and subtracting the amount of starch in the AIS.

Enzymatic extraction of pectin

To 1 part of pomace 19 pans of 0.1 m sodium acetate buffer of pH 5.0 (with 0.02% $NAN_3$) is added. At 30° C. the mixture is treated for 20 hours with solutions of the purified endo-β-1,4-glucanase according to the invention. Afterwards the mixture is filtered and the pomace residues washed with 10 parts of distilled water.

The AIS is obtained in the way described above.

Results

With the chemical extraction 17.5% pectin was obtained whereas with the enzymatic extraction between 8 and 10.5% were obtained, depending upon the amount of endo-β-1,4-glucanase used.

These results prove, that the endo-β-1,4-glucanase is one of the key enzymes for enzymatic extraction of pectins from plant material. Also, it appears from the above that 45 to 60% of the pectin extractable by chemical means and with all the accompanying disadvantages can be extracted enzymatically in an environmental sound manner.

---

We claim:

1. A substantially pure Endo-β-1,4-glucanase, which is immunologically reactive with an antibody raised against a purified endo-β-1,4-glucanase endogenous to *Aspergillus aculeatus,* strain CBS 101.43, wherein said substantially pure endo-β-1,4-glucanase comprises a partial amino acid sequence having the amino acid sequence of Seq. ID. NO 1.

2. The purified endo-β-1,4-glucanase of claim 1 which further exhibits a pH-optimum of 2.0–4.0, an isoelectric point of 2.0–3.5, a molecular weight of between 30,000 and 50,000, and a temperature optimum between 30° and 70° C.

3. An isolated DNA segment endogenous to *Aspergillus aculeatus* strain CBS 101.43 that comprises the DNA sequence of Seq. ID NO :5 and that encodes an endogenous endo-β-1,4-glucanase.

4. An isolated DNA construct comprising the endo-β-1,4-glucanase encoding DNA segment of claim 3 and that further comprises in operable linkage with said endo-β-1,4-glucanase coding region a transcriptional promoter, a region encoding a signal or leader peptide, and a transcriptional terminator.

5. A vector comprising the DNA construct of claim 4.

6. A vector according to claim 5, wherein the DNA construct comprises the *Aspergillus oryzae* taka amylase promoter.

7. A transformed host cell comprising the vector according to claim 5.

8. Transformed host cell according to claim 5, wherein the transformed host is an Aspergillus strain.

9. A transformed host cell according to claim 7, wherein the transformed host is a strain selected from the species: *Aspergillus aculeatus, Aspergillus niger, Aspergillus oryzae* or *Aspergillus awamori*.

10. A transformed host cell according to claim 7, wherein the transformed host is a microorganism which in its non-transformed condition does not produce endo-β-1,4-glucanase or only produces endo-β-1,4-glucanase in insignificant amounts.

11. A method for producing a substantially pure endo-β-1,4-glucanase comprising culturing the transformed host cell of claim 8 under conditions conducive for expression of the endo-β-1,4-glucanase coding region of the DNA construct and purifying the expressed endo-β-1,4-glucanase from the culture medium.

12. A substantially pure endo-β-1,4-glucanase produced by the method of claim 11.

* * * * *